| United States Patent [19] | [11] | 4,389,397 |
|---|---|---|
| Lo et al. | [45] | Jun. 21, 1983 |

[54] SOLUBILIZATION OF IVERMECTIN IN WATER

[75] Inventors: Pak-Kan A. Lo, Edison; James B. Williams, Freehold, both of N.J.

[73] Assignee: Merck & Co., Inc., Rahway, N.J.

[21] Appl. No.: 304,124

[22] Filed: Sep. 21, 1981

Related U.S. Application Data

[63] Continuation-in-part of Ser. No. 174,957, Aug. 4, 1980, abandoned.

[51] Int. Cl.$^3$ ............................................. A61K 31/70
[52] U.S. Cl. ....................................... 424/180; 424/279
[58] Field of Search ................................. 424/180, 279

[56] References Cited

U.S. PATENT DOCUMENTS

| 4,093,629 | 6/1978 | Fisher | 424/279 X |
| 4,171,314 | 10/1979 | Chabala et al. | 424/279 X |
| 4,173,571 | 11/1979 | Chabala et al. | 424/279 X |
| 4,199,569 | 4/1980 | Chabala et al. | 424/180 |
| 4,200,581 | 4/1980 | Fisher et al. | 424/180 |
| 4,201,861 | 5/1980 | Mrozik et al. | 424/180 X |
| 4,203,976 | 5/1980 | Fisher et al. | 424/180 |
| 4,206,205 | 6/1980 | Mrozik et al. | 424/180 |

OTHER PUBLICATIONS

Chemical Abstracts, 86:34289s (1977), [Sato, T., et al., Japan. Kokai 76,112,509, 10/5/76].
Chemical Abstracts, 90:12219z (1979), [Burelova, A., et al., Farm. Obz. 1977, 46(2), 69–80].
Spiegel et al., Journal of Pharmaceutical Sciences, vol. 52, pp. 917–927 (1963).

Primary Examiner—Richard A. Schwartz
Attorney, Agent, or Firm—David L. Rose; Mario A. Monaco

[57] ABSTRACT

Ivermectin, an antiparasitic agent which is insoluble and unstable in water, is solubilized by the formation of colloidal particles, called micelles, with surface active agents as solubilizers and stabilized by using cosolvents and/or appropriate substrates in the aqueous formulation. The liquid formulations are suitable for use as parenteral or oral administration for the treatment of parasitic infections.

6 Claims, No Drawings

SOLUBILIZATION OF IVERMECTIN IN WATER

CROSS REFERENCE TO RELATED APPLICATIONS

This application is a continuation-in-part of our patent application Ser. No. 174,957, filed Aug. 4, 1980, now abandoned.

BACKGROUND OF THE INVENTION

Ivermectin and the avermectin family, of which ivermectin is a member, is a series of new and very potent antiparasitic agents which are useful against a broad spectrum of endoparasites and ectoparasites in mammals as well as having agricultural uses against various parasites found in and on crops and in soil. Ivermectin is disclosed in U.S. Pat. No. 4,199,569, issued Apr. 22, 1980 to Chabala and Fisher. Ivermectin is a mixture, in the ratio of approximately 80:20 of 22,23-dihydro C-076 B1a and B1b. In administering ivermectin to animals it is most convenient for parenteral formulations to use an aqueous solution. Non-aqueous solutions tend to cause irritation and tissue damage at the injection site; precipitate the active ingredient at the injection site, have higher viscosity and poorer syringability; and generally have a higher cost. Aqueous liquid formulations for oral use are also preferred over non-aqueous formulations because non-aqueous solvents tend to have an unacceptable taste.

Thus, it is desirable to prepare an aqueous liquid formulation of ivermectin. However, ivermectin has very poor solubility in water, at a level of about 0.005 mg per ml at room temperature.

Ivermectin can be solubilized using surface active agents as solubilizers. This results in the formation of micelles, or minute colloidal particles which surround the ivermectin molecule, isolating it from the water, but forming a clear solution in the water. Such a solution does contain sufficient active ingredient in order to prepare liquid formulations, for oral or parenteral use. However, it was discovered that such micelle formulations were unstable and the ivermectin degraded at such a rate as to render the shelf life inadequate for a commercial preparation.

It was unexpectedly discovered during the investigation of this instability that the use of certain cosolvents and/or substrates would reduce the instability and result in an aqueous liquid solution which is suitable for parenteral or oral administration, and which had adequate shelf life such that a viable commercial preparation was afforded.

Ivermectin is a member of a family of compounds identified as avermectins. The basic avermectin compounds are isolated from the fermentation broth of the microorganism *Streptomyces avermitilis*. Such compounds are described in British Pat. No. 1,573,955. In addition, certain derivatives of these basic fermentation products have been prepared.

Some of the avermectins contain a 22,23-double bond. This may be selectively reduced to prepare the ivermectin compounds discussed above. In addition, the avermectins possess a disaccharide moiety at the 13-position consisting of the α-L-oleandrosyl-α-L-oleandrosyl group. One or both of these saccharide groups may be removed as described in U.S. Pat. No. 4,206,205. The thus produced aglycone derivatives have a hydroxy group at the 13-position. This group may be removed to form the 13-deoxy compound as described in U.S. Pat. Nos. 4,171,314 and 4,173,571. On the avermectin compounds and derivatives are several hydroxy groups which may be acylated as described in U.S. Pat. No. 4,201,861.

It is anticipated that the process and formulation of the instant invention can be carried out on the foregoing compounds since all such compounds share to a varying degree, the aqueous instability of the ivermectin compound.

In addition, a series of compounds identified as milbemycin compounds have the same 16 membered macrocyclic ring as do the avermectin compounds, although they do not have the disaccharide moiety and also differ in other substituent groups. These compounds are disclosed in U.S. Pat. No. 3,950,360 and they also would be expected to benefit from the stabilizing effects of the instant process and formulations.

SUMMARY OF THE INVENTION

The instant invention concerns the solubilization and stabilization of avermectin compounds generally and in particular ivermectin, a new anthelmintic agent, using surface active agents to dissolve the avermectin or ivermectin, and certain cosolvents and substrates to stabilize the thus formed micelle solution. Thus, it is an object of this invention to describe such a solution. A further object is to describe the parenteral and oral formulations which can be prepared using such a solution. A still further object is to describe the solubilizing agents, cosolvents and substrates which are employed in such solutions and formulations. Further objects will become apparent from a reading of the following description.

DESCRIPTION OF THE INVENTION

The instant invention resides in the unexpected stabilization of an aqueous solution of ivermectin or other avermectin compound prepared from water and a surface active agent, wherein one or both of a cosolvent and a substrate are added. The cosolvent and the substrate individually reduce the instability of the ivermectin solution, however, the combination of both the cosolvent and the substrate are found to surprisingly increase the stability of the solution even further.

The aqueous solution is initially formed by dissolving the avermectin in a pharmacologically acceptable surfactant. A different surfactant will be employed depending upon the parenteral or oral acceptability of the final formulation.

For parenteral use a pharmacologically acceptable non-ionic surfactant will be employed. Examples of such non-ionic surfactants will be polyoxyethylated vegetable oils, polyoxyethylene sorbitan monoisostearate, polyoxyethylene sorbitan monostearate, polyoxyethylene sorbitan monooleate (also known as polysorbate 80 or Tween 80) and the like. The preferred surface active agent is polysorbate 80.

For oral use, a pharmacologically acceptable non-ionic surfactant or an anionic surfactant will be employed. The non-ionic surfactants used for the parenteral formulation may also be employed for the oral formulation, and again polysorbate 80 is preferred. For anionic surfactants examples of such will be dioctylsodium sulfosuccinate (also known as Aerosol OT) and the like.

The preferred anionic surfactant is dioctylsodium sulfosuccinate. The most preferred of the non-ionic and anionic surfactants is polysorbate 80.

The aqueous solution of the avermectin and the surface active agent is prepared by dissolving the avermectin in the surface active agent such that the surface active agent will constitute from 0.5 to b 25% w/v preferably from 4 to 25% w/v of the final solution. The ivermectin is present in different amounts for parenteral and oral uses. For parenteral formulations the avermectin is present at from 0.1 to 7.5% w/v and for oral formulations the avermectin is present in from 0.01 to 2.0% w/v. Water may then be added to the surfactant solution to form a clear solution.

The cosolvents which are employed and which have been found to dramatically increase the stability of the avermectin are water miscible organic solvents which are suitable for parenteral or oral administration. Examples of such cosolvents are glycerol formal, propylene glycol, glycerine, polyethylene glycol and the like. The preferred cosolvent is glycerol formal for parenteral administration and propylene glycol for oral administration. The cosolvents are added to the final formulation to the extent of 10 to 60% v/v preferably from 10 to 40% v/v of the final formulation.

The substrates which are used to stabilize the formulation, either alone or in combination with the cosolvent are benzyl alcohol, lidocaine, parabens, choline, and the like. Benzyl alcohol and lidocaine are the preferred substrates and both have been used in a single formulation with acceptable results. The substrates are present in the final formulations at a concentration of from about 1 to 5% w/v. Benzyl alcohol is specifically present at about 1 to 5% v/v and lidocaine is present at about 1 to 4% w/v.

The preferred process for preparing the formulation is to combine the avermectin in a mixture of the surface active agent, the cosolvent and the substrate. At this time also buffering agents and other adjuvants which assist in the final formulation may be added. Water is then added to the desired volume, or almost the desired volume, and the pH adjusted, if necessary, to a range of 6.0 and 6.5 for optimum stability. The final volume is adjusted to the desired amount and the solution sterilized by autoclaving or membrane filtration.

The stability of the avermectin aqueous solution is thus greatly improved through the use of the above-described cosolvents and substrates. Without such cosolvents and substrates, the solution of the avermectin formed by combining the drug in a surfactant and adding water, is observed to have a 50% stability per month at room temperature. That is 50% of the ivermectin is lost after only one month. By combining a cosolvent or a substrate with the surfactant, the stability is seen to dramatically increase to about 90% in 2 to 3 months; or about 5% loss of ivermectin activity per month. When both the cosolvent and the substrate are used in the surfactant formulation the stability of the resultant aqueous formulation is seen to even more dramatically increase its stability to more than 95% in 2 to 3 years. That is, over a period of 2 to 3 years, less than 5% of the active ingredient is lost.

The reason behind this dramatic and unexpected stabilizing effects resulting from the use of the cosolvent and the substrate are not completely understood. While we do not wish to be bound by theory it appears that in the initial micelle formation with the avermectin and the substrate, water is still able to penetrate the micelle, or otherwise contact the avermectin, even though it is surrounded by the surface active agent. The cosolvent and the substrate apparently displace the water of hydration of the micelle and further isolate the avermectin from the water which contacts the outside surface of the micelle, thus reducing the reaction of the water upon the avermectin and increasing the stability of the resultant solution.

The resultant solution avoids all of the disadvantages of non-aqueous formulations while retaining the required attributes of a parenteral or oral formulation. The solution is stable, both chemically and physically; it is low in viscosity, therefore its syringability is excellent; it does not cause any irritation or tissue damage at the injection site; its taste is not objectionable upon oral administration; at most concentrations the solution is totally dilutable with water without precipitating the avermectin; the avermectin is rapidly absorbed; and the solution is produced at low cost.

Thus, the unexpected stability of the instant aqueous solution as provided by the instant avermectin is seen to provide for a totally acceptable formulation for parenteral or oral administration.

The following examples are given generally referring to ivermectin. However, it should be appreciated that the instant process and formulation will be equally applicable to other avermectin compounds and derivatives including milbemycin-type compounds. The following compounds will be suitable in the instant process and formulation:

Avermectin A1a and A1b;
Avermectin B1a and B1b;
Avermectin B1a and B1b aglycone;
5-acetyl-22,23-dihydro avermectin B1a and B1b;
5-acetyl avermectin B1a and B1b;
13-deoxy-22,23-dihydro avermectin B1a and B1b aglycone.

The following examples of aqueous formulations using the instant invention are provided in order that the invention might be more fully understood. They are not to be construed as limitative of the invention.

EXAMPLE 1

| Ivermectin Injectable Solution (10 mg/mL) | |
|---|---|
| Formula | |
| Ivermectin | 1.0% w/v |
| TWEEN 80 | 8% w/v |
| Glycerol Formal | 20% w/v |
| Lidocaine | 2% w/v |
| Benzyl Alcohol | 1% v/v |
| Water for Injection | q.s. 100% v/v |
| pH adjusted to 6.2 using 1N HCl | |

Procedure

1. Dissolve ivermectin and lidocaine in TWEEN 80, glycerol formal, and benzyl alcohol.
2. Add water for injection equal to 80% of final volume.
3. Adjust pH of the solution to 6.2 using 1 N HCl.
4. Adjust the solution to volume with water for injection.
5. Sterilize by autoclave or membrane filtration and package aseptically.

Following the above procedure, using avermectin B1a and B1b in an approximately 80:20 mixture in place of ivermectin, there is obtained a stabilized aqueous formulation thereof.

EXAMPLE 2

| Ivermectin Injectable Solution (20 mg/mL) | |
|---|---|
| Formula | |
| Ivermectin | 2.0% w/v |
| TWEEN 80 | 12% w/v |
| Glycerol Formal | 25% v/v |
| Benzyl Alcohol | 3% v/v |
| Sodium phosphate Dibasic-Anhydrous | 0.1% w/v |
| Sodium Phosphate Monobasic-Monohydrate | 0.9% w/v |
| Water for Injection | q.s. 100% w/v |

Procedure

1. Dissolve ivermectin in TWEEN 80, glycerol formal, and benzyl alcohol.
2. Disperse the buffer salts into the solution.
3. Add water for injection and agitate until a clear solution is obtained.
4. Adjust the solution to volume with water for injection.
5. Sterilize by autoclave or membrane filtration and package aseptically.

Following the above procedure using avermectin B1a and B1b in an approximately 80:20 mixture, there is obtained a stabilized aqueous formulation thereof.

EXAMPLE 3

| Ivermectin Oral Solution (0.8 mg/mL) | |
|---|---|
| Formula | |
| Ivermectin | 0.08% w/v |
| TWEEN 80 | 8.0% w/v |
| Propylene Glycol | 20% v/v |
| Benzyl Alcohol | 3% v/v |
| Sodium Phosphate Dibasic-Anhydrous | 0.1% w/v |
| Sodium Phosphate Monobasic-Monohydrate | 0.9% w/v |
| Water, Purified | q.s. 100% w/v |

Procedure

1. Dissolve ivermectin in TWEEN 80, propylene glycol, and benzyl alcohol.
2. Disperse the buffer salts into the solution.
3. Add purified water and agitate until a clear solution is obtained.
4. Adjust the solution to volume with purified water and package.

Following the above procedure, using avermectin A1a and A1b, or avermectin B1a and B1in an approximately 80:20 mixture, or there is obtained a stabilized aqueous formulation thereof.

What is claimed is:

1. A stabilized aqueous formulation which comprises from 0.1 to 7.5% w/v of an avermectin for parenteral administration or from 0.01 to 2.0% w/v of an avermectin for oral administration; from 0.5 to 2.5% of a surface active agent selected from polyoxyethylene sorbitan monoisostearate, polyoxyethylene sorbitan monostearate and polysorbate 80; from 10 to 60% of a cosolvent selected from glycerol formal, glycerine and polyethyleneglycol; and from 1 to 5% w/v of a substrate selected from benzyl alcohol, lidocaine, parabens and choline.

2. A stabilized aqueous formulation of claim 1 wherein the avermectin is ivermectin.

3. The stabilized aqueous formulation of claim 1 wherein the surface active agent is present at from 4 to 25% w/v and the cosolvent is present at from 10 to 40% v/v.

4. The stabilized aqueous formulation of claim 2 wherein the surface active agent is polysorbate 80; the cosolvent is glycerol formal; and the substrate is benzyl alcohol or lidocaine.

5. The stabilized aqueous formulation of claim 1 which is prepared for parenteral administration.

6. The stabilized aqueous formulation of claim 1 which is prepared for oral administration.

* * * * *

UNITED STATES PATENT AND TRADEMARK OFFICE
CERTIFICATE OF CORRECTION

PATENT NO. : 4,389,397
DATED : June 21, 1983
INVENTOR(S) : P.A. Lo, J.B. Williams It is certified that error appears in the above-identified patent and that said Letters Patent is hereby corrected as shown below:

In column 6 line 18 delete "2.5%" and insert -- 25% --.

Signed and Sealed this

Sixteenth Day of May, 1989

*Attest:*

DONALD J. QUIGG

*Attesting Officer*  *Commissioner of Patents and Trademarks*